(12) United States Patent
Chavez-Taniwangsa et al.

(10) Patent No.: US 12,023,269 B2
(45) Date of Patent: Jul. 2, 2024

(54) ASSEMBLY INCLUDING INTERLOCKED COMPONENTS

(71) Applicant: Ossur Iceland ehf, Reykjavik (IS)

(72) Inventors: Juan Chavez-Taniwangsa, Foothill Ranch, CA (US); Marcos Vargas, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 350 days.

(21) Appl. No.: 16/044,830

(22) Filed: Jul. 25, 2018

(65) Prior Publication Data
US 2019/0029862 A1 Jan. 31, 2019

Related U.S. Application Data

(60) Provisional application No. 62/537,585, filed on Jul. 27, 2017.

(51) Int. Cl.
*A61F 5/01* (2006.01)

(52) U.S. Cl.
CPC .............. *A61F 5/0123* (2013.01); *A61F 5/01* (2013.01); *A61F 2210/0076* (2013.01)

(58) Field of Classification Search
CPC .......... A61F 5/01; A61F 5/118; A61F 5/0111; A61F 5/0106; A61F 5/0102; A61F 5/0127; A61F 5/013; A61F 5/0123; A61F 2005/0165; A61F 2220/0025; A61F 2210/0076; F16B 7/04; F16B 5/0056; F16B 2012/103; F16B 2/20; F16B 21/06; A44B 11/00

USPC ......... 403/345, 354, 355; 24/31 R, 305, 307, 24/326, 572.1, 163 R, 454; 602/5, 23, 26, 602/78

See application file for complete search history.

(56) References Cited

U.S. PATENT DOCUMENTS

| | | | |
|---|---|---|---|
| 4,856,501 A * | 8/1989 | Castillo ................. | A61F 5/0123 602/16 |
| 5,792,086 A * | 8/1998 | Bleau .................... | A61F 5/0123 602/26 |
| 6,299,588 B1 * | 10/2001 | Fratrick ................ | A61F 5/0127 24/625 |
| 7,479,122 B2 | 1/2009 | Ceriani et al. | |
| 7,727,174 B2 | 6/2010 | Chang et al. | |
| 7,941,867 B2 | 5/2011 | Olson | |
| 8,043,244 B2 | 10/2011 | Einarsson et al. | |
| 8,048,013 B2 | 11/2011 | Ingimundarson et al. | |

(Continued)

FOREIGN PATENT DOCUMENTS

DE  102012024167 A1  6/2014
WO     0202038 A1  1/2002

OTHER PUBLICATIONS

International Search Report from PCT Application No. PCT/US2018/043653, dated Nov. 27, 2018.

*Primary Examiner* — Caitlin A Carreiro
(74) *Attorney, Agent, or Firm* — Workman Nydegger (57) ABSTRACT

An assembly comprises a first component having a first structure, and a second component having a second structure corresponding to the first structure. The first and second structures form interlocking profiles. A third component extends over the first and second structures, with the third component maintaining the first and second structures together to form an interlocked section.

16 Claims, 5 Drawing Sheets

(56) References Cited

U.S. PATENT DOCUMENTS

| | | |
|---|---|---|
| 8,282,588 B2 | 10/2012 | Ingimundarson et al. |
| 8,292,838 B2 | 10/2012 | Ingimundarson et al. |
| 8,506,866 B2 | 8/2013 | Deseure et al. |
| 8,512,267 B2 | 8/2013 | McCune et al. |
| 8,679,044 B2 | 3/2014 | Thorgilsdottir et al. |
| 8,740,829 B2 | 6/2014 | Lee et al. |
| 9,323,221 B2 | 4/2016 | Villar et al. |
| 9,370,911 B2 | 6/2016 | Maurice |
| 9,375,341 B2 | 6/2016 | Ingimundarson et al. |
| 9,399,337 B2 | 7/2016 | Curnutt |
| 9,474,334 B2 | 10/2016 | Jonsson et al. |
| 9,498,025 B2 | 11/2016 | Omarsson et al. |
| 9,668,907 B2 | 6/2017 | Romo et al. |
| 2003/0044231 A1* | 3/2003 | Anvick ............... F16B 5/0056 403/354 |
| 2003/0060745 A1 | 3/2003 | Seligman |
| 2005/0148915 A1* | 7/2005 | Nathanson ............ A61F 5/0123 602/16 |
| 2005/0187505 A1 | 8/2005 | Carlson |
| 2008/0195013 A1* | 8/2008 | Ingimundarson ..... A61F 5/0123 602/26 |
| 2009/0240181 A1* | 9/2009 | Sreeramagiri ........ A61F 5/0123 602/26 |
| 2012/0177927 A1 | 7/2012 | Cheng |
| 2013/0331751 A1* | 12/2013 | Lee ...................... A61F 5/0125 602/5 |
| 2014/0261229 A1 | 9/2014 | Bao et al. |
| 2015/0150708 A1* | 6/2015 | Paez .................... A61F 5/0123 602/16 |
| 2016/0008157 A1* | 1/2016 | Brookover ........... A61F 5/0123 602/26 |
| 2016/0081838 A1 | 3/2016 | Ledezma et al. |
| 2016/0206448 A1 | 7/2016 | Klutts |
| 2016/0250782 A1 | 9/2016 | Krass et al. |
| 2016/0271901 A1 | 9/2016 | Demange |
| 2016/0297183 A1 | 10/2016 | Demange et al. |
| 2016/0361189 A1 | 12/2016 | Campbell et al. |
| 2017/0189241 A1 | 7/2017 | Joseph |

* cited by examiner

ASSEMBLY INCLUDING INTERLOCKED COMPONENTS

FIELD OF THE DISCLOSURE

The field of the disclosure relates to an assembly, and more particularly to an assembly formed from at least two components interlocked or secured to one another. The at least two components may be formed from different materials having different properties relative to one another, such as an assembly in an orthopedic device.

BACKGROUND

In manufacturing goods, components of an assembly are often secured to one another by fasteners. The modification of components to accommodate fasteners and the step of applying fasteners adds extra time, cost, and effort to manufacturing efforts. The fasteners add to bulk and weight of an assembly. Therefore, it is desirable to eliminate fasteners in assembling components while minimizing weight and bulk to an assembly.

Customization of an assembly may be desirable for a given application, although materials used for the components may be harmful for handling or cumbersome. When handling sheets or frame elements comprising an uncured resin impregnated fiber, particularly while the resin is curing, the process for forming the sheets or frame elements with the curing resin may be messy. The individual shaping the frame element is exposed to the curing resin, and the individual may lack the skill to cleanly shape the frame element. Upon curing of the resin, the frame element may require post-processing to provide a finished surface for actual use by a user. Therefore it is desirable to provide means for protecting the frame element during fabrication, while offering means for providing a finished surface upon post-processing.

A drawback to using fasteners is the inability to easily or quickly remove a component from another component in an assembly. When using an assembly, it is desirable to provide a system for removably attaching one component to another, while assuring the components will remain secured to one another during use. An example occurs in orthopedic devices whereby an intermediate fastener for removable attachment, such as with hook and loop systems, is used to hold one component relative to another. The intermediate fastener may deteriorate over use or is generally cumbersome to use since it must be sufficiently robust to hold the components to one another. Therefore, it is desirable to provide an assembled structure that can repeatedly endure removing and attaching of one component to another in a simple manner that does not lead to deterioration of the component.

There is further a problem of assemblies of two or more components being difficult to disassemble as needed. An example occurs in orthopedic devices, wherein if a liner on a frame element is difficult to detach and remove, such as for periodic cleaning, the result can be unsanitary conditions, discomfort, and shortened use of assemblies.

There is a problem of manufacturing assemblies of two or more components requiring extensive post-processing and/or finishing steps. This can be problematic when less-skilled workers produce the assembly or if the products are assembled in the field, and which may add to the cost of manufacturing and reduce the quality of products.

There is a need for an assembly of two or more components that reduces costs and complications in manufacturing, while improving upon cumbersome fastening devices and means.

SUMMARY

The embodiments of the disclosure are arranged for overcoming the drawbacks in assembled structures in the prior art.

The embodiments relate to an assembly, and more particularly to an assembly formed from at least two components interlocked or secured to one another. The at least two components may be formed from different materials having different properties relative to one another. The at least two components may be permanently secured to one another or removably secured to one another.

According to an embodiment, the assembly includes a first component having a first structure, a second component having a second structure corresponding to the first structure. The first and second structures form first and second interlocking profiles such that the first and second structures interlock with one another. A third component extends over the first and second structures, and the third component maintains the first and second structures together to form an interlocked section. The third component may extend over an entirety of the interlocked section.

The first interlocking profile of the first structure may define an opening adapted for receiving the second interlocking profile of the second structure having corresponding features for insertion into the opening. The opening of the first structure defines a main opening, and the second structure has a head portion adapted to be received by the main opening. The first structure further defines a channel leading to the opening, and the second structure has a shaft. The channel may be arranged in a shape for receiving the shaft.

The first structure may define a base portion arranged to be received by shoulder portions of the second structure. The shaft extends from the shoulder portions, and the channel extends inwardly of the base portion. The first component may be formed from a different material than the second component. The first and second components may be formed from at least one metal material, and the third component may be formed from a polymeric material.

The assembly may have a fourth component extending over a frame portion of the first component. The frame portion may define a frame opening, and the fourth component may form at least one opening corresponding to the frame opening. The frame opening may define a different shape from the at least one opening of the fourth component, and the at least one opening may overlie the frame opening. The frame portion may define an aperture, and the fourth component may define an aperture corresponding in shape to the aperture. The assembly may define a gap along the first component between the third and fourth components.

Another embodiment of the assembly has a first component defining a periphery, and a second component forming a cavity defined by a cavity periphery. The second component is adapted to cover the periphery of the first component, and the second component may only cover a first side of the first component. A third component is adapted to cover a second side of the first component, and a profile of the third component may cover an entirety of the second side of the first component.

The first component may receive a fourth component, such that the first component has a receptacle for receiving the fourth component. The second component may interlock with the first and fourth components to maintain the fourth component in place relative to the first component. The periphery of the first component defines a beveled edge over which the cavity periphery extends to a second surface of the first component. The second and the third components may be secured to one another along their peripheries to surround the first component.

Another embodiment entails an assembly with a first component having a peripheral segment, and a second component having a peripheral lip extending about the peripheral segment and having opposed peripheral edges. The peripheral lip defines opposed lip portions forming a channel therebetween. The peripheral lip may clamp onto the first component, and extend about the peripheral segment leaving a width of a first surface of the first component devoid of the second component. The opposed lip portions may define an irregular width extending over a first surface of the first component. The second component may terminate at a location short of a total length of the first component. The first component may define a coupling part located outside of the location and is devoid of the second component. The second component is preferably detachable from the first component.

Additional features and advantages of the disclosure will be set forth in the description that follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

The drawing figures are not necessarily drawn to scale, but instead are drawn to provide a better understanding of the components, and are not intended to be limiting in scope, but to provide exemplary illustrations. The figures illustrate exemplary configurations of an assembly, and in no way limit the structures or configurations of an assembly and components according to the present disclosure.

DETAILED DESCRIPTION OF VARIOUS EMBODIMENTS

Figure 1:
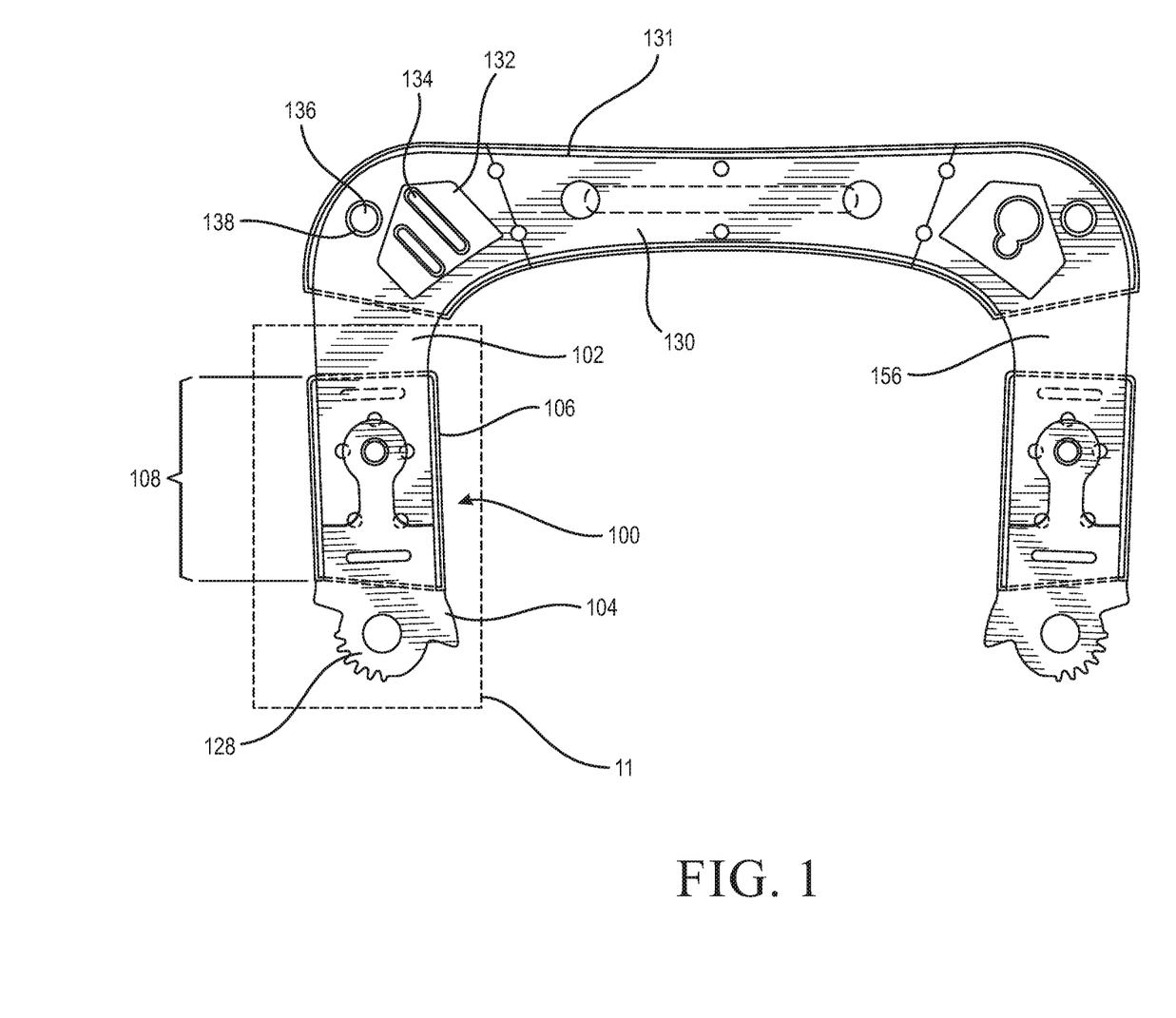
FIG. 1 is a plan view showing a first embodiment of an assembled structure.
Figure 2:
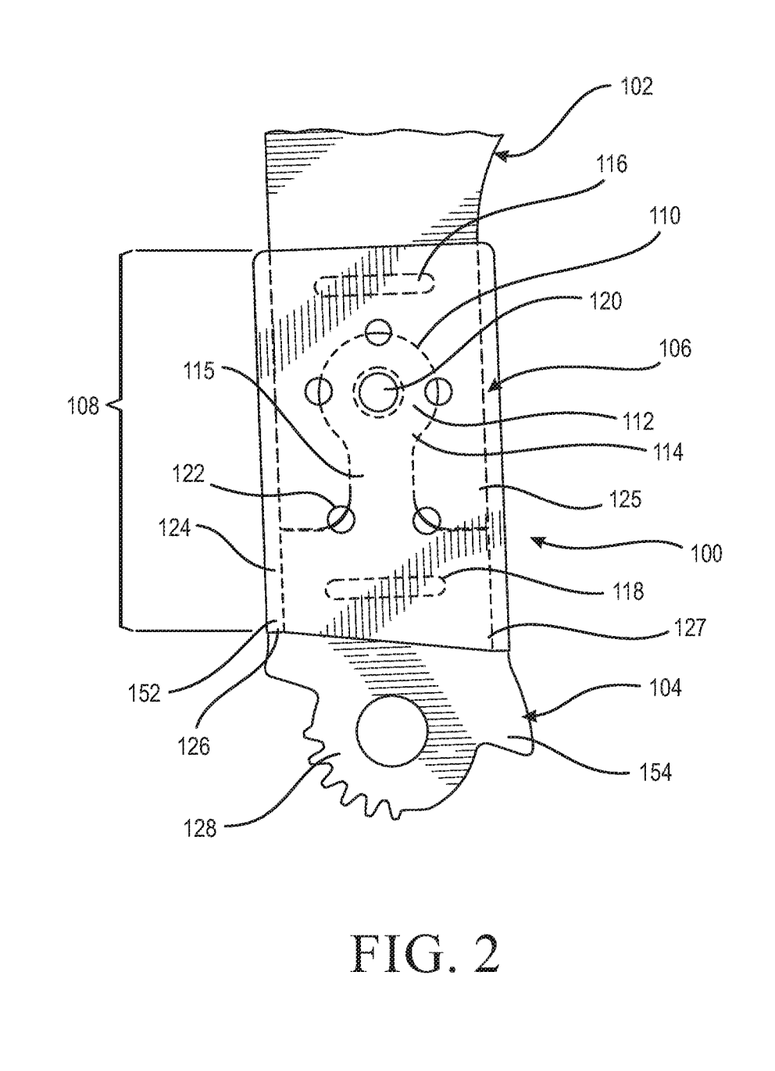
FIG. 2 is a detail view showing detail II in FIG. 1.
Figure 3:
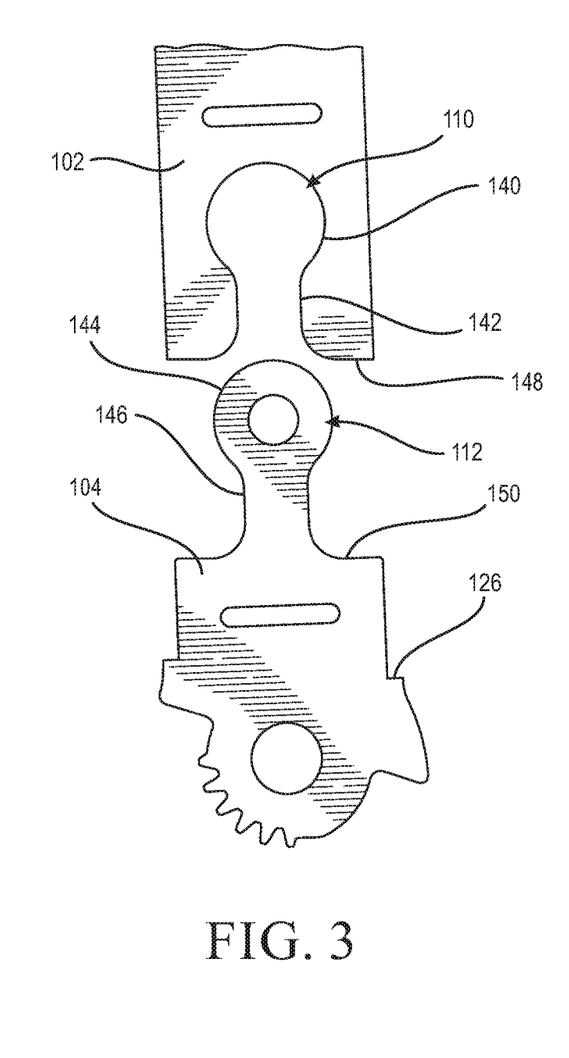
FIG. 3 is a schematic exploded view showing the first and second components in FIG. 1.

According to the embodiment of FIGS. 1-3, an assembly 100 comprises a first component 102 having a first structure 110, a second component 104 having a second structure 112 corresponding to the first structure 110, and a third component 106 extending over the first and second structures 110, 112. As shown, the first component 102 forms a frame for an orthopedic device, and the second component 104 forms a hinge connection in an orthopedic device. An example of an orthopedic device in which the frame and hinge may be found in taught in U.S. patent application publication no. 2016/0008157, published on Jan. 14, 2016, and incorporated by reference.

In this example, a frame can be constructed without needing to account for the design and material requirements of a hinge connection used in the orthopedic device. The second component 104 may be formed from a complicated geometry, and the first component 102 can be constructed from a simpler geometry. This facilitates the construction of the first component, and allows for more detail on a smaller part, as in the second component 104 forming the hinge component.

The first and second components 102, 104 may be formed from different materials, and the interlocked structure enables the use of these different materials in an orthopedic device by taking advantage of the beneficial properties of each of these materials for specific uses. The first component 102 or frame may be constructed from a metal such as aluminum or a resin impregnated with fibers, such as carbon fiber, and taking advantage of the lightweight nature, relative affordability, and malleability of such materials. The second component 104 may be constructed from steel which is advantageously more durable when meshing or cooperating with a corresponding hinge connection carried by another frame of the orthopedic device. Using an interlocked structure advantageously allows for optimized manufacturing—reduced costs of materials, simplified manufacturing processes, and optimal use of material properties for optimal functionality, without sacrificing structural integrity.

Either of the first and second components 102, 104 may be formed from structural materials such as aluminum, steel, magnesium, titanium or from a composite such as a resin impregnated with structural fibers. As discussed, the first and second components 102, 104 can be constructed from different materials, or they can constructed from the same material.

The first and second structures 110, 112 preferably interlock with one another and form an interlocked structure 108. The first and second structures 110, 112, form first and second interlocking profiles 114, 115 such that the first and second structures 110, 112 are interlocked with one another in the interlocked structure 108. The third component 106 maintains the first and second structures 110, 112 together in the interlocked structure 108.

The interlocked structure may be formed from many corresponding geometries between the first and second components 102, 104, and generally comprises complementary structures between the first and second components 102, 104 that fit with one another. The first interlocking profile 114 of the first structure 110 defines an opening denoted by reference numbers 140, 142 adapted for receiving the second interlocking profile 115 of the second structure 112 having corresponding features denoted by 144, 146 for inserting into the opening 140, 142. The opening of the first structure 110 defines a main opening 140, and the second structure 112 has a head portion 144 adapted to be received by the main opening 140. The first structure 110 further defines a channel 142 leading to the main opening 140, and the second structure 112 has a shaft 146. The channel 142 is arranged in shape for receiving the shaft 146. The first structure 110 defines a base portion 148 arranged to be received by shoulder portions 150 of the second structure 112, and the shaft 146 extends from the shoulder portions 150, and the channel 142 extends inwardly of the base portion 148.

The interlocked structure 108 may be sufficient by itself to secure the first and second components 102, 104 to one another. The tolerances on the first and second structures 110, 112 may be sufficiently tight to enable the first and second structures 110, 112 to be secured together by being press-fitted into one another. The interlocked structure 108 may further include an adhesive or at least one fastener to keep the interlocked structure 108 in position if the connection between the first and second structures 110, 112 is insufficient by itself.

In the illustrated embodiment, the interlocked structure 108 is further held in place by the third component 106, which is molded or overmolded at least over the interlocked structure 108. The term "overmold" has its ordinary meaning and refers to material that is added over an existing article or material. Overmolding is generally understood as a process where a single part is created using two or more different materials in combination. In the instant disclosure, the interlocked structure may be considered such single part.

The third component 106 preferably extends over an entirety of the interlocked structure 108, such as by forming a sleeve, or may cover a portion of the interlocked structure 108 where needed to further reinforce the connection of the first and second structures 110, 112 at the interlocked structure 108. In a preferred embodiment, the third component 106 is formed from a plastic, such as a rigid plastic including ABS, PA6, PC, PE, PP, POM, PS or a blend of such plastics, or other suitable plastic or fiber reinforced plastics.

The third component 106 may not be restricted to covering the interlocked structure 108, but may engage either or both first and second components 102, 104 to form a rigid structure therewith. The third component 106 may be a structure maintaining the first and second structures 110, 112 in place, or as a glue securing the first and second structures 110, 112 together.

In the depicted embodiment, the first and second components 102, 104 form at least one opening 116, 118, 120 through which material of the third component 106 extends to interlock with the first and second components 102, 104, and securely holding the first and second components 102, 104 in place. The third component 106 may be molded over the interlocked structure 108, and may define at least one opening 122 exposing at least one of the first and second components 102, 104 resulting from molding or functionally exposing the interlocked structure 108.

When constructed as a sleeve, the third component 106 defines a side or edge portion 124 extending beyond peripheral walls 125, 127 of the first and second components 102, 104. A width of the third component 106 is preferably greater than widths of the first and second components 102, 104 within the interlocked section 108. The second component 104 may define a ledge portion 126 outside the interlocked section 108 adapted to receive an end portion 152 of the third component 106. The side or edge portion 124 is flush with the ledge portion 126 such that a periphery 154 of the second component 104 extends outwardly relative to the side or edge portion 124.

The periphery 154 of the second component 104 below the third component 106 may form a hinge component 128. The extent of which the third component 106 extends over the interlocked structure 108 can be controlled during manufacturing, and serve both to functionally maintain or protect the first and second structures 110, 112, and further to minimize interaction with other components, such as the hinge component 128 in an orthopedic device.

The general concept of covering one component with another is also exemplified in a fourth component 130 that extends over a frame portion 131 of the first component 102. In this embodiment, the fourth component 130 can cover peripheral edges of the first component 102, which may be rough or unfinished, and add a more user-friendly surface, such as in an orthopedic device.

Besides merely covering a frame portion, the fourth component 130 may also customize features of the orthopedic device. The frame portion 131 may define a frame opening 132, and the fourth component 130 may form at least one opening 134 corresponding to the frame opening 132. In the illustrated example, the frame opening 132 can be a generic opening provided to accommodate various features in the fourth component 130, and the at least one opening 134 of the fourth component 130 can be tailored to a particular use. This example enables the at least one opening 134 to serve as slots for receiving a strap, with the frame opening 132 being formed sufficiently generically to allow for the at least one opening 134 to take different shapes depending on usage.

Another example of how the features of the frame portion 131 can correspond to the features in the fourth component 130 is provided by an aperture 136 in the frame portion 131 that preferably closely aligns with an aperture 138 in the fourth component 130. The aperture 138 of the fourth component 130 can be tailored to be larger or smaller than the aperture 136 in the frame portion 131. The aperture 138 may be sized larger than the aperture 136, such that the material of the fourth component 130, such as a plastic, is more resilient than the material of the frame portion 131. A snap fitting may secure to the aperture 138 and engage due to the resilience of the material of the fourth component 130, whereas the material of the frame portion 131 does not yield to the snap fitting because of its lower resilience.

As shown, the fourth component 130 may have a width greater than a width of the frame portion 131. The first component 102 may define a gap between the third and fourth components 106, 130, thereby exposing the first component 102. The gap defined in this example by the first component 102 may advantageously allow a clinician to adjust the configuration of the orthopedic frame to better fit a wearer and/or facilitate various other attachments, such as straps, tensioning devices, spacers, and other devices suitable for an orthopedic device.

Figures 4, 5:
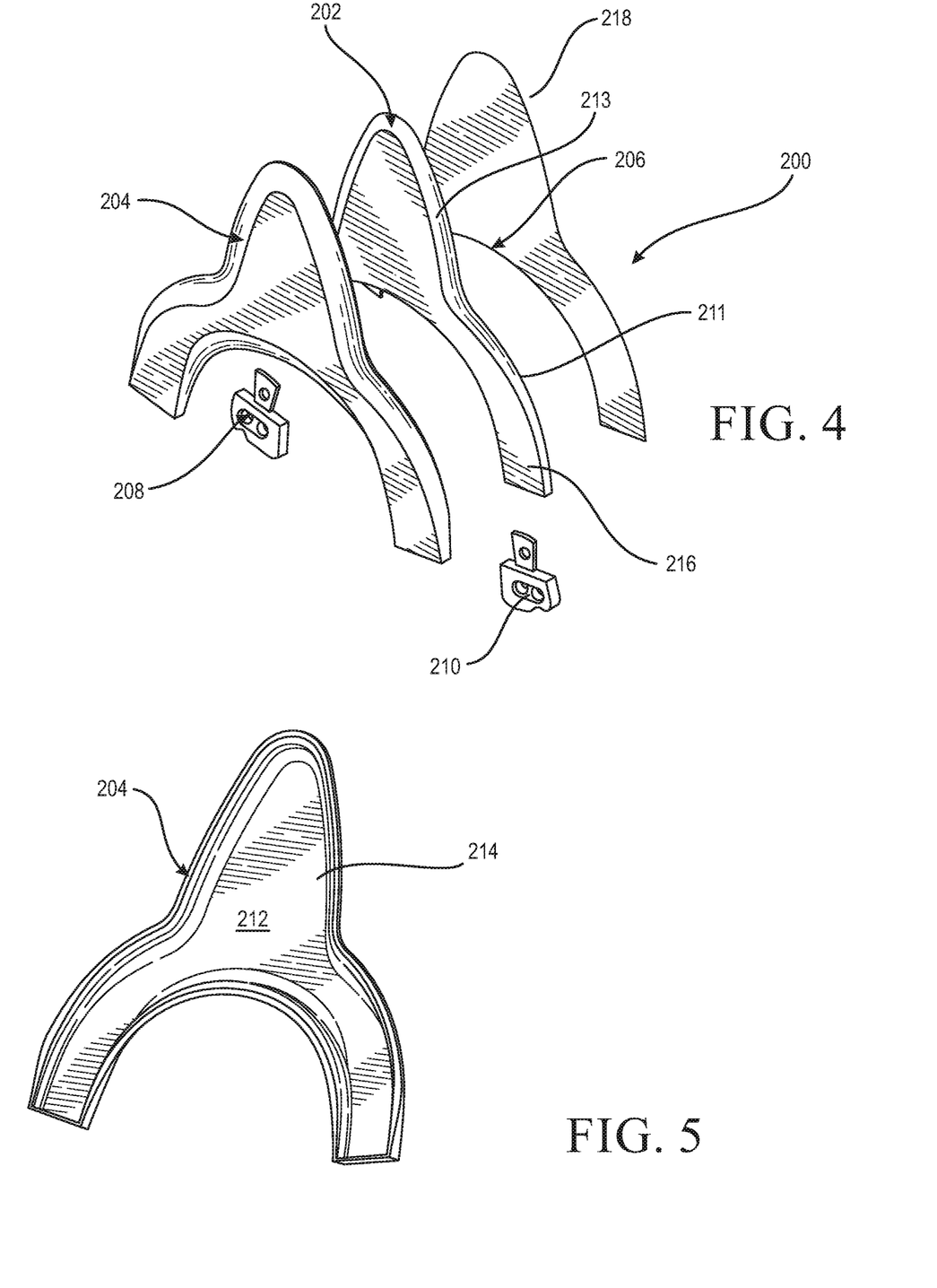
FIG. 4 is an exploded view showing a second assembled structure.
FIG. 5 is a perspective view showing an interior of a second component in FIG. 5.
Figure 6:
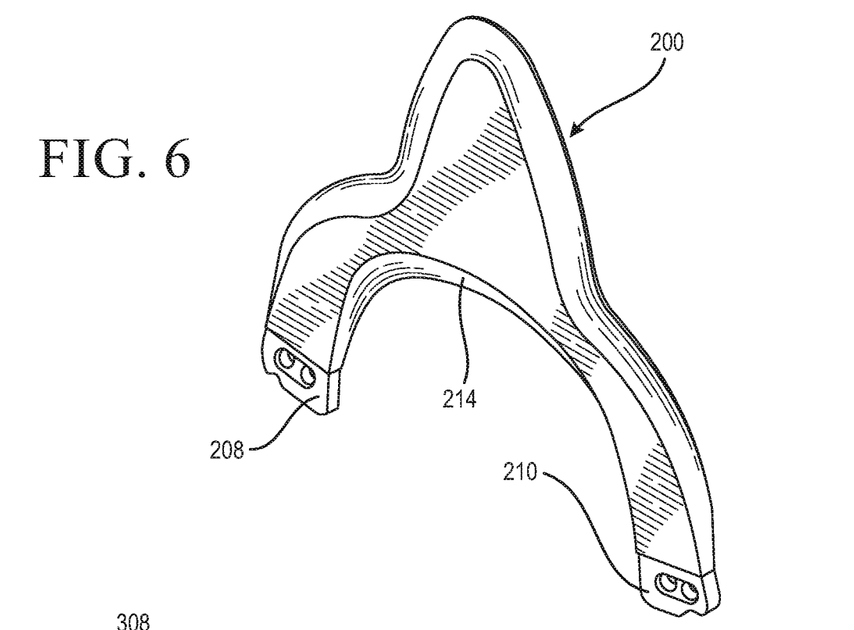
FIG. 6 is an assembled view of the second assembled structure of FIG. 4.

Referring to the embodiment of FIGS. 4-6, an assembly among different components can contain a first component 202 by second and third components 204, 206. In this embodiment, the first component 202 may be a frame portion comprising an uncured or partially cured resin impregnated with fibers. The second and third components 204, 206 can contain the first component 202, such as like a bag, so that during shaping of the first component 202, any residue from the resin is contained within or by the second and third components 204, 206. This arrangement is advantageous in that the resin may be activated in the field and shaping of the first component 202 may be made by individuals with less skill, or in more accessible environments.

While the first component 202 may be formable into or is a structurally rigid structure, the second and third components 204, 206 may be substantially more flexible than the first component 202, without hindering formation of the first component 202, but retaining their shape according to a definitive shape of the first component 202. This advantageously provides a soft, flexible outer surface for the first component 202 with no post-processing or other finishing steps.

An example of applicability of this embodiment may be found in making a custom-fit orthopedic device, such as in U.S. patent application publication no. 2016/0008157, published Jan. 14, 2016, or U.S. Pat. No. 8,048,013, granted Nov. 1, 2011, and incorporated herein by reference.

In an example, the assembly 200 includes the first component 202 having a periphery 211, and the second component 204 having a cavity 212 defined by a cavity periphery 214 so the second component 202 is adapted to cover the periphery 211 of the first component 202. The third component 206 may be adapted to cover a second side of the first component 202, to enclose the first component 202 between the second and third components 204, 206.

The second component 204 only covers a first side of the first component 202, although it may form a three-dimensional shape in that it can extend about peripheral edges of the first component 202. The third component 206 covers an entirety of the second side of the first component 202, and may form a planar shape to merely cover a surface of the first component 202. However, the second and third components 204, 206 may define different configurations aside from or in combinations of the configurations discussed above. The second and third components 204, 206 may form a clamshell configuration.

The first component 202 may receive a fourth component 208, 210, such as in attachments for a hinge connection in an orthopedic device. The first component 202 may have a receptacle 216 for receiving the fourth component 210. The second component 204 may interlock with the first and fourth components 202, 208, 210 to maintain the fourth component 208, 210 in place relative to the first component 202. The fourth component 208, 210 may be formed from metal inserts or from a material different from at least the first component 202, such as a glass-fill with overmold onto steel.

The second and third components 204, 206 may be attached to the first component 202 at different stages of fabricating the assembly 200. The first component periphery 211 may define a beveled edge 213 over which the cavity periphery 214 extends to the second surface of the first component 202. The second component 204 may be molded over the first component 202 or pre-formed and then attached to the first component 202. The third component 206 may be molded onto the first component 202 or otherwise secured to the second component 204 so that the second and the third components 204, 206 are secured to one another along their peripheries to surround the first component 202.

While the first component 202 has been discussed as preferably being a pre-impregnated composite, exemplary materials that may be used for constructing the first component 202 include metals such as aluminum, titanium, and steel, thermoset resin composite systems including glass or carbon fibers, and thermoplastics rendered rigid by way of material composition and geometry of the frame members. The second and third components 204, 206 are preferably plastic, such as a thermoplastic.

Figure 7:
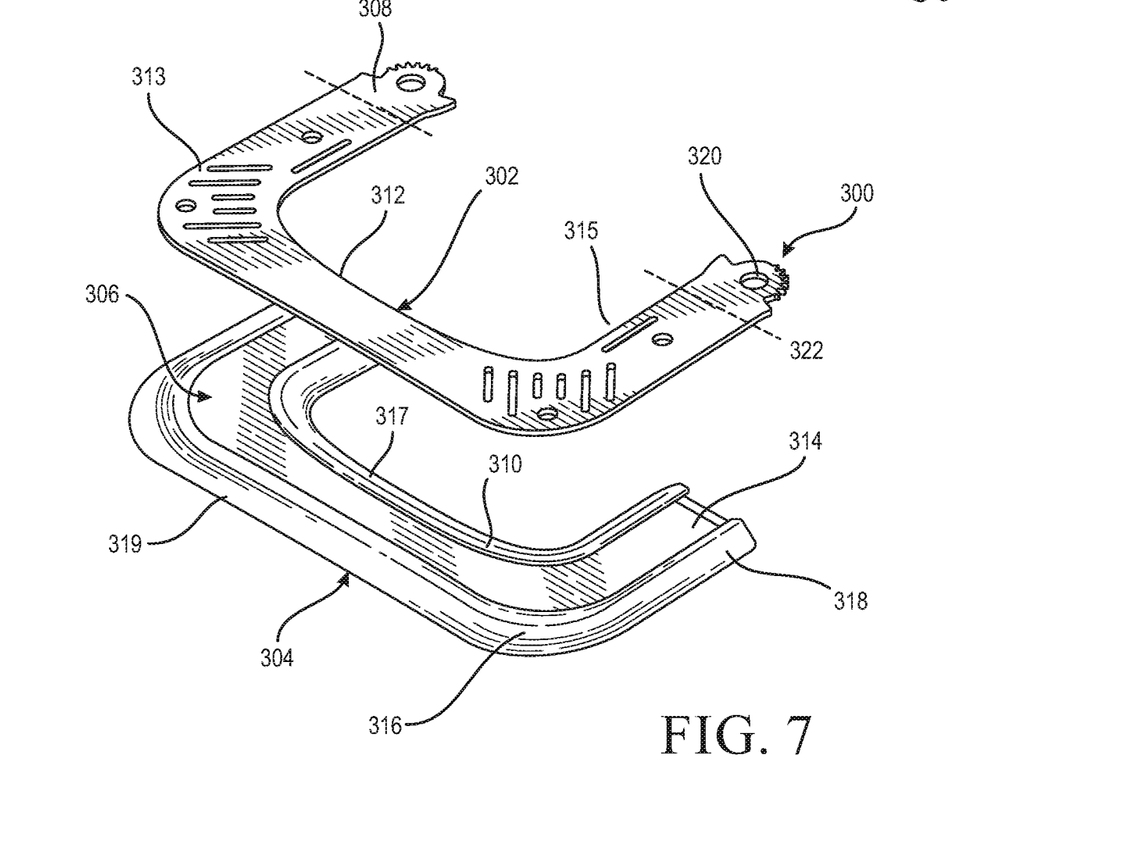
FIG. 7 is a partial exploded view showing a third assembled structure.
Figure 8:
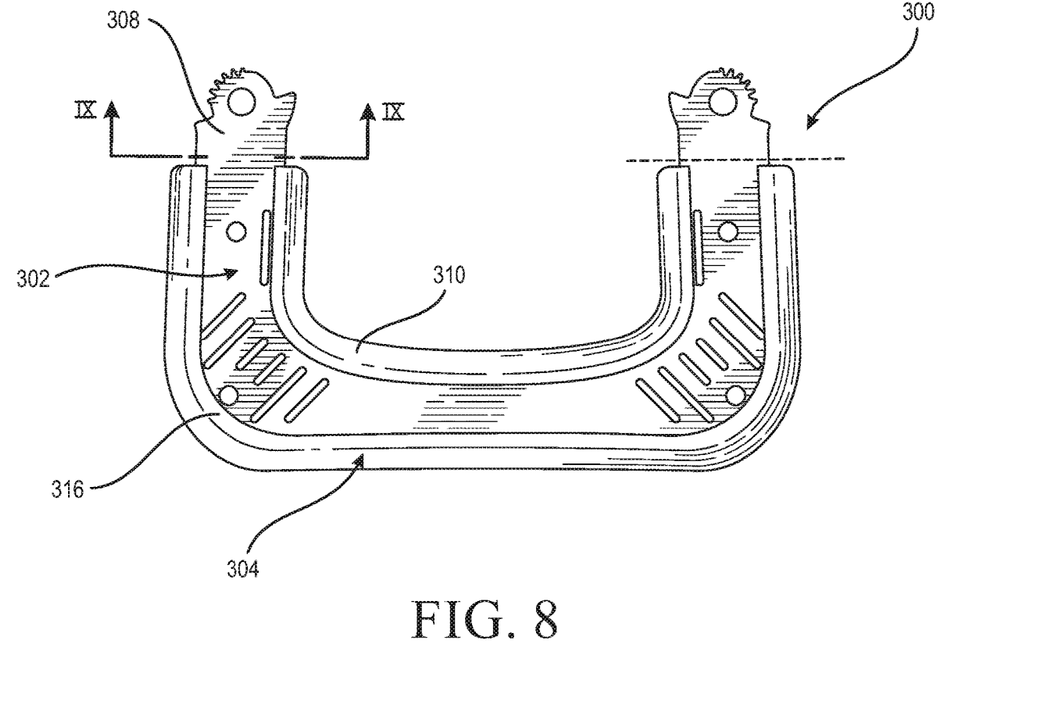
FIG. 8 is an assembled view of the third assembled structure of FIG. 7.
Figure 9:
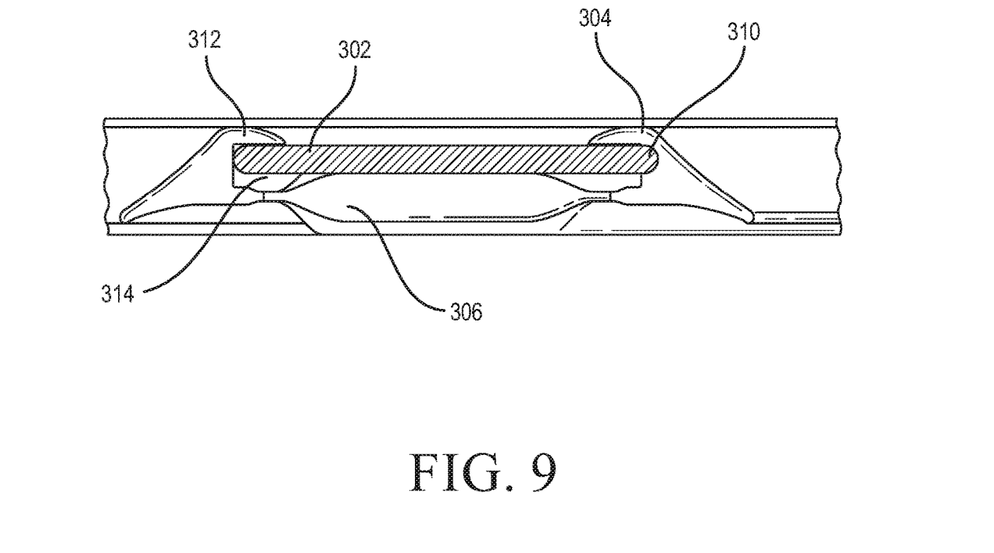
FIG. 9 is a cross-sectional view along line IX-IX in FIG. 8.

FIGS. 7-9 show another embodiment of the disclosure wherein an assembly 300 includes a first component 302 having a peripheral segment 312, and a second component 304 having a peripheral lip 310 extending about the peripheral segment 312. In this embodiment, the assembly 300 may reflect an orthopedic device, such as the first component 302 being a frame as in U.S. patent application publication no. 2016/0008157, whereby the second component 304 is a spacer or padding feature that is removably secured to the frame.

In the assembly 300, the peripheral segment 312 preferably has opposed peripheral edges 313, 315. The peripheral lip 310 defines opposed lip portions 317, 319, and the opposed lip portions 317, 319 define a channel therebetween 314. The peripheral lip 310 preferably clamps onto the first component 302. The peripheral lip 310 may only extend about the peripheral segment 312 and leave a width of a first surface of the first component 302 devoid of the second component 304, this width devoid of the second component 304 being defined by a terminal end 318 of the second component 304. The opposed lip portions 317, 319 may define an irregular width in expanded edging 316 extending over a first surface of the first component 302, to reinforce an area of the first component, such as at corners in FIG. 8. The expanded edging 316 may further advantageously provide enhanced control, such as better leverage/grip, in facilitation of addition and removal of the second component 304 to/from the first component 302.

A third component 306 may be defined within the channel 314, such that the second and third components 304, 306 form a composite structure. The second component 304 may form a frame for the third component 306, and be formed from a flexible plastic, such as a thermoplastic elastomer that is overmolded onto the third component 306, which may be a foam laminate or other suitable material. The composite structure effectively forms a padding that can be removably attached to the first component 302 or frame without the necessity of fasteners.

As shown in FIG. 9, a second surface of the first component 302 is preferably adjacent to the third component 306, whereas the second surface of the first component 302 extends along the third component 306. The second component 304 may be retained onto the peripheral segment 312 of the first component 302. The first component 302 may define a region outside the second component 304, and the second component 304 may terminate at a location 308 short of a total length of the first component 302. The first component 302 may define a coupling part 320 located outside of the location 308 and devoid of the second component 304.

The assembly described reduces costs and complications of manufacturing, optimizes the properties of individual components, and improves quality of assemblies due to the ability to use optimal materials for individual components without sacrificing structural integrity. The assembly also solves problems associated with fastening devices. The assembly further improves upon the ability of the assembly to be conveniently disassembled without sacrificing beneficial structural properties, and reduces the number of post-processing and/or finishing steps.

It is to be understood that not necessarily all objects or advantages may be achieved under any embodiment of the disclosure. For example, those skilled in the art will recognize that the assembly may be embodied or carried out in a manner that achieves or optimizes one advantage or group of advantages as taught herein without achieving other objects or advantages as taught or suggested.

The skilled artisan will recognize the interchangeability of various disclosed features. Besides the variations described herein, other known equivalents for each feature can be mixed and matched by one of ordinary skill in this art to construct an assembly under principles of the present disclosure. It will be understood by the skilled artisan that the features described may be adapted to other types of devices.

Hence this disclosure and the embodiments and variations thereof are not limited to assemblies used in orthopedic devices, but can be utilized in any devices making use of assemblies as described.

Although this disclosure describes certain exemplary embodiments and examples of different assemblies, such as those that can be used in an orthopedic device, it therefore will be understood by those skilled in the art that the present disclosure extends beyond the specifically disclosed knee brace embodiments to other alternative embodiments and/or uses of the disclosure and obvious modifications and equivalents thereof. It is intended that the scope of the present disclosure should not be limited by the particular disclosed embodiments described above, and may be extended to other applications that may employ the features described herein.

The invention claimed is:

1. An assembly comprising:
   a first component having a first structure;
   a second component having a second structure corresponding to the first structure, the first and second structures forming first and second interlocking profiles such that the first and second structures interlock with one another and are secured to one another along their peripheries, the first and second interlocking profiles being defined between opposing peripheral side walls of the first and second components;
   a third component consisting of a single, continuous sleeve having first and second opposed sides and extending over the first and second structures, the sleeve maintaining the first and second structures together to form a rigid interlocked section and keeping the first and second components in position relative to one another, the sleeve having first and second opposed and open end portions, and first and second closed and opposite peripheral edge portions, the peripheral edge portions being closed along the opposing peripheral side walls of the first and second components;
   wherein the first interlocking profile of the first structure defines an opening adapted for receiving at least a portion of the second interlocking profile of the second structure, the opening including a main opening and a channel leading to the main opening, the channel having a width that is less than a width of the main opening;
   wherein the first and second components form at least one opening through which material of the sleeve extends continuously from and between both the first and second opposed sides of the sleeve for interlocking with the first and second components;
   wherein the sleeve is formed from a polymeric material and is overmolded as a single part over the interlocked section;
   wherein a width of the sleeve is greater than widths of the first and second components within the interlocked section, the first and second peripheral edge portions of the sleeve extend beyond, around and over the opposing peripheral side walls of the first and second components, wherein the sleeve extends over an entirety of the interlocked section.

2. The assembly of claim 1, wherein the second interlocking profile of the second structure has corresponding features for insertion into the opening.

3. The assembly of claim 2, wherein the second structure has a head portion adapted to be received by the main opening.

4. The assembly of claim 3, wherein the second structure has a shaft, the channel being arranged in shape for receiving the shaft.

5. The assembly of claim 4, wherein the first structure defines a base portion arranged to be received by shoulder portions of the second structure, the shaft extending from the shoulder portions, and the channel extending inwardly of the base portion,
   wherein the sleeve extends beyond and around both the base portion of the first structure and shoulder portions of the second structure.

6. The assembly of claim 3, wherein the channel has a width that is less than a width of the head of the second structure.

7. The assembly of claim 4, wherein the shaft of the second structure has a width that is less than a width of the head of the second structure.

8. The assembly of claim 1, further comprising a fourth component extending over a frame portion of the first component.

9. The assembly of claim 8, wherein the frame portion defines a frame opening, the fourth component forming at least one opening corresponding to the frame opening.

10. The assembly of claim 9, wherein the frame opening defines a different shape from the at least one opening of the fourth component, the at least one opening overlying the frame opening.

11. The assembly of claim 8, wherein the frame portion defines an aperture, and the fourth component defines an aperture, the aperture of the fourth component corresponding in shape to the aperture of the frame portion.

12. The assembly of claim 8, wherein the assembly defines a gap along the first component between the third and fourth components.

13. The assembly of claim 1, wherein the first component is formed from a different material than the second component.

14. The assembly of claim 1, wherein the first and second components are formed from at least one metal material.

15. The assembly of claim 1, wherein tolerances of the first and second structures are sufficiently tight to enable the first and second structures to be secured together by the second structure being press-fitted into the first structure.

16. The assembly of claim 1, wherein the second component defines a ledge portion outside the interlocked section receiving a first end portion of the sleeve, the first edge portion being flush with the ledge portion, such that a periphery of the second component beyond the interlocked section extends outwardly relative to the first edge portion.

* * * * *